US00PP23787P3

(12) United States Plant Patent
Schoone

(10) Patent No.: US PP23,787 P3
(45) Date of Patent: Jul. 30, 2013

(54) *PHALAENOPSIS* ORCHID PLANT NAMED '146833'

(50) Latin Name: *Phalaenopsis hybrida*
Varietal Denomination: 146833

(75) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 0 days.

(21) Appl. No.: 13/067,336

(22) Filed: May 25, 2011

(65) Prior Publication Data

US 2012/0102608 P1 Apr. 26, 2012

(30) Foreign Application Priority Data

Oct. 20, 2010 (NL) ..... OPS711

(51) Int. Cl.
*A01H 5/00* (2006.01)

(52) U.S. Cl.
USPC ..... Plt./311

(58) Field of Classification Search
USPC ..... Plt./311
See application file for complete search history.

*Primary Examiner* — Kent L Bell
(74) *Attorney, Agent, or Firm* — Foley & Lardner LLP

(57) ABSTRACT

A new and distinct *Phalaenopsis* plant named '146833' particularly characterized by flowers which are pink/purple with some yellow in the labellum; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: '146833'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name '146833'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* '146833' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* '146833' originated from a cross made by the inventor in 1998 in Strengweg, Heemskerk, The Netherlands. The female or seed parent is the *Phalaenopsis* cultivar designated 'Leen Boon', unpatented. The male or pollen parent is the *Phalaenopsis* cultivar designated 'Love Goofy', unpatented. The new *Phalaenopsis* '146833' was discovered and selected by the inventor as a single flowering plant within the progeny of the stated cross in a controlled environment in 2006 in Strengweg, Heemskerk, The Netherlands.

Asexual reproduction of the new *Phalaenopsis* cultivar by tissue culture was first performed in January, 2006 in Cieweg 13, Heemskerk, The Netherlands, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be unique characteristics of '146833', which in combination distinguish this *Phalaenopsis* as a new and distinct cultivar:

1. flowers which are pink/purple with some yellow in the labellum;
2. plant produces more than one inflorescence;
3. plants may be propagated economically and uniformly using tissue culture;

4. inflorescence is long and sturdy
5. relatively short, dark-green foliage

Presently, there is no other commercial cultivar to which '146833' can be meaningfully compared.

The claimed variety '146833' differs from its male parent ('Love Goofy') and female parent ('Leen Boon') in that '146833' has more intense pink flowers than the pink flowers of the parent varieties, and '146833' has larger flowers than either parent variety.

BRIEF DESCRIPTION OF THE PHOTOGRAPHS

The accompanying photographs illustrate the overall appearance of the new *Phalaenopsis* '146833' showing the colors as true as is reasonably possible with colored reproductions of this type. Colors in the photographs may differ slightly from the color values cited in the detailed botanical description, which accurately describe the color of '146833'.

DETAILED BOTANICAL DESCRIPTION

Figure 1:
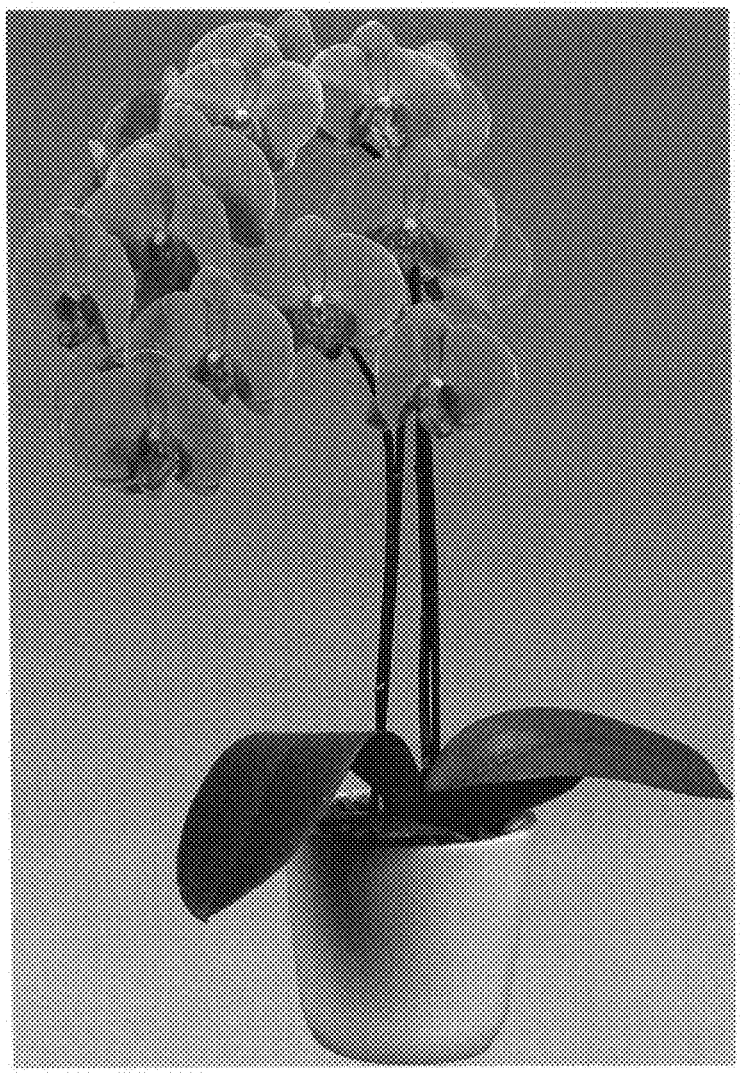
FIG. 1 shows a side view perspective of a typical flowering plant of '146833' in a 12 cm pot, at 16 months of age.

The new *Phalaenopsis* cultivar '146833' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of '146833' as grown in a greenhouse in Strengweg, Heemskerk, The Netherlands, under conditions which closely approximate those generally used in commercial practice. Initially, the ideal temperature to grow plants of '146833' is 27° C. during the day and at night. Then, during the flowering phase of '146833', the ideal growing temperature is 20-22° C. during the day and 18° C. at night. Light levels for growing '146833' are a minimum of 5,000 lux and a maximum of 10,000 lux. A balanced fertilizer with level of 200 ppm N, 87 ppm P, 168 ppm K is applied. Duration of growth of '146833' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the '146833' plants described is 12 months after potting.

Classification:

*Botanical.—Phalaenopsis hybrida.*

Parentage:

*Female or seed parent.—Phalaenopsis* cultivar designated 'Leen Boon', unpatented.

*Male or pollen parent.—Phalaenopsis* cultivar designated 'Love Goofy', unpatented.

Propagation:

*Type.*—Tissue culture.

*Rooting habit and description.*—Fleshy; approximately 5 mm-7 mm wide and green in color; freely branching. It takes 12 weeks for plants growing in tissue culture to initiate roots.

Plant:

*Size at maturity.*—Height: about 66 cm. Spread: about 60 cm to 65 cm.

*Growth habit.*—Standard; dark-green leaves and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 peduncles with flowers appear.

Foliage:

*Quantity per plant.*—About 6 to 8 leaves are produced before flowering.

*Arrangement and attachment.*—Half up/horizontal and on two sides.

*Overall shape of leaf.*—Oval, the tip is blunt and asymmetric.

*Texture.*—Smooth and leathery.

*Pubescence.*—3 to 4 pairs of leaves.

*Mature leaf length.*—About 21 cm and 23 cm.

*Mature leaf width.*—About 8 cm to 9 cm.

*Mature leaf thickness.*—About 2 mm.

*Mature leaf color.*—Upper side: RHS N137A; lower side: RHS 137B.

*Venation.*—Pattern: parallel. Color of midvein (both sides): dark green (RHS N137A).

Peduncle:

*Quantity per plant.*—About 1 to 2.

*Number of flowers per peduncle.*—About 10 to 23.

*Length.*—About 65 cm to 78 cm.

*Diameter.*—About 7 mm.

*Strength.*—Strong.

*Aspect.*—Upright.

*Texture.*—Glabrous and smooth.

*Color.*—Dark brown with green (some RHS N200A and RHS 189A and some RHS 145B, all colors individually present.).

*Internode.*—Length: about 40 to 50 mm.

Inflorescence description:

*Appearance.*—Upright to slightly pendant, racemose inflorescence with bilaterally symmetrical flowers that open in succession beginning with the lowermost flower.

*Buds.*—Height (from base to tip): about 15 to 22 mm. Diameter (at midpoint): about 13 to 19 mm. Shape: egg-shaped. Color: RHS 77A.

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with about 16 to 20 flower buds and flowers per inflorescence. First flowers can be expected approximately 4 to 6 months after planting a plant with a leaf diameter of 3 to 5 cm. Flowers persistent.

*Flowering longevity.*—On the plant: about 4 to 6 months; lastingness of cut flowers: has not been observed.

*Fragrance.*—No fragrance.

Figure 2:
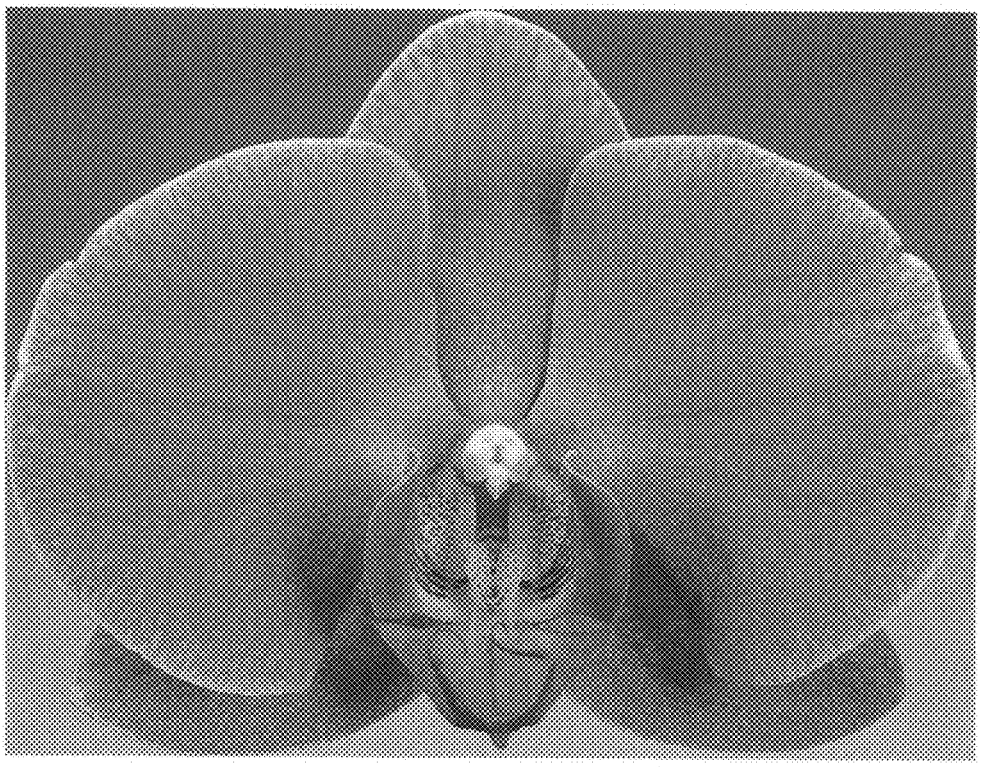
FIG. 2 shows a close-up view of the typical buds and flowers of '146833'.
Figure 3:
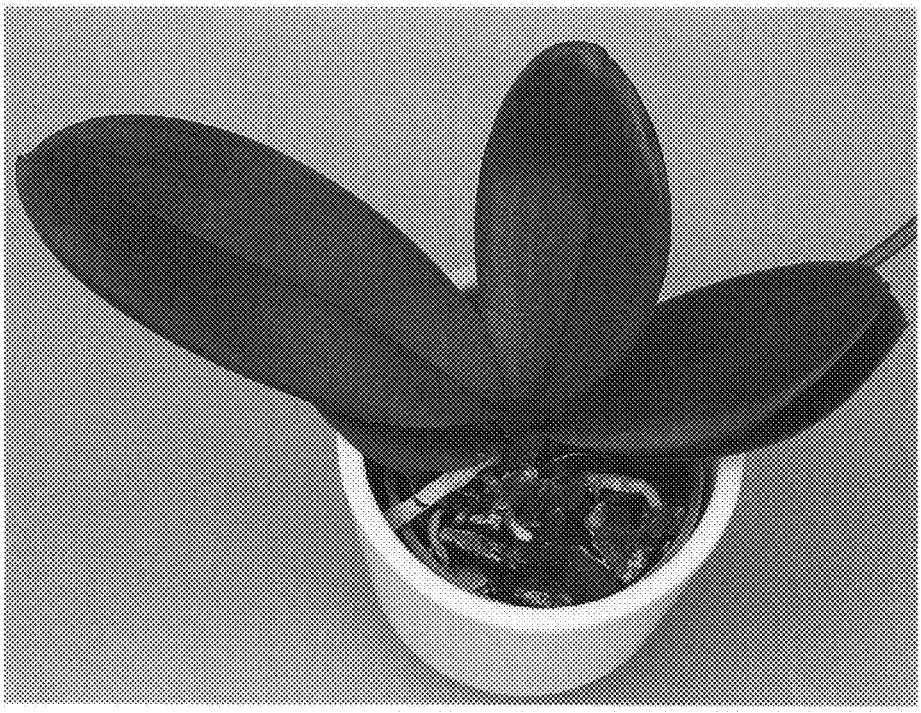
FIG. 3 shows a close-up view of the typical leaves of '146833'.

*Flower.*—Rate of opening: Flowers fully opened about 2 to 3 days after tepal separation. Orientation at opening: slanted upward and outward. Shape: see FIG. 2. Size: Height: about 70 mm. Diameter: about 95 mm. Depth of tube: about 18 mm.

*Tepals*.—Quantity and arrangement: six tepals that are trimerous, overlapping and arranged in 2 whorls. Petals are more pronounced than sepals.

*Petals*.—Arrangement: Inner whorl of petals comprises 3 petals, 2 lateral petals and labellum. 2 lateral petals: Overall shape: broadly ovate and weakly cupped. Apex: oval. Margin: weakly undulate. Length: about 55 mm. Width: about 40 mm. Texture: Upper surface: smooth and satiny. Under surface: smooth and satiny. Color (when fully opened): upper side: purple RHS N78 B. lower side: purple RHS N78 C. Labellum: Overall shape: 3-lobed with 2 prominent callosities at central junction of the lateral lobes and base of the midlobe. Lateral lobes of labellum fold upward about the column; the midlobe extends forward and is terminated by 2 short filiform appendages at the apex. Lateral lobes of the labellum are ovate in shape while the midlobe is triangular with a bump and a rib on it. Margin: entire and weakly undulate. Length: about 30 mm. Width (not flattened): about 26 mm. Texture: Upper and lower surface: smooth and satiny. Color (when fully opened): Upper surface: Main color is purple/violet RHS N81A. The base of the lateral lobes is white (RHS NN155C) with purple/red stripes and spots (RHS 64A). Lower surface: main color is purple/violet RHS N81A. At the base of the lateral lobes is some white (RHS NN155B). The pestle is yellow/orange (RHS 23A) with red/purple spots and stripes (RHS 64A). Chirri is purple/violet (RHS N81A) and the column is purple (RHS N78D) and white (RHS NN155B). Chirri: normal. Pestle (callosities): Length: about 5 mm. Width: about 6 mm.

*Sepals*.—Arrangement: Outer whorl of sepals comprises 3 sepals. Overall shape: elliptical and weakly cupped. Length: about 42 mm. Width: about 30 mm to 35 mm. Texture: Upper and lower surface: smooth and satiny. Color (when fully opened): upper surface: purple RHS N78B. Lower surface: purple RHS N78C.

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 14 mm. Diameter: about 6 mm. Color: purple (RHS N78D) and white (RHS NN155B).

*Pollinia*.—Quantity: Two. Size: 1 mm. Color: yellow/orange RHS 23A.

*Ovary*.—Length: about 5 mm. Diameter: about 6 mm. Color: white (RHS NN155C) with some purple (RHS N78D).

*Pedicel*.—Length: about 45 mm to 50 mm. Diameter: about 4 mm. Color: green (RHS 138C) and close to the flower some purple (RHS 77D).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named '146833', as illustrated and described herein.

* * * * *

UNITED STATES PATENT AND TRADEMARK OFFICE

CERTIFICATE OF CORRECTION

PATENT NO. : PP23,787 P3
APPLICATION NO. : 13/067336
DATED : July 30, 2013
INVENTOR(S) : René Schoone It is certified that error appears in the above-identified patent and that said Letters Patent is hereby corrected as shown below:

ON THE TITLE PAGE:

Item (54) and in the Specification, Col. 1, the title should read:
--PHALAENOPSIS ORCHID PLANT NAMED 'FLOR146833'--

Item (50) the technical information should read:
--(50) Latin Name: *Phalaenopsis hybrid*
Varietal Denomination: FLOR146833--

IN THE ABSTRACT:

Item (57) the abstract should read:
--(57) ABSTRACT

A new and distinct *Phalaenopsis* plant named 'FLOR146833' particularly characterized by flowers which are pink/purple with some yellow in the labellum; plants which may be propagated economically and uniformly using tissue culture; plants which produce more than one inflorescence; long and sturdy inflorescences; and relatively short, dark-green foliage.--

IN THE SPECIFICATION:

At Col. 1, line 3, "'146833'" should read --'FLOR146833'--

At Col. 1, line 10, "'146833'" should read --'FLOR146833'--

At Col. 2, line 1, "'146833'" should read --'FLOR146833'--

At Col. 2, line 9, "'146833'" should read --'FLOR146833'--

At Col. 2, line 14, "'146833'" should read --'FLOR146833'--

Signed and Sealed this
Twenty-fifth Day of February, 2014

Michelle K. Lee

Michelle K. Lee
*Deputy Director of the United States Patent and Trademark Office*

At Col. 2, line 30, "'146833'" should read --'FLOR146833'--

At Col. 3, line 4, "'146833'" should read --'FLOR146833'--

At Col. 3, line 5, "'146833'" should read --'FLOR146833'--

At Col. 3, line 7, "'146833'" should read --'FLOR146833'--

At Col. 3, line 8, "'146833'" should read --'FLOR146833'--

At Col. 3, line 15, "'146833'" should read --'FLOR146833'--

At Col. 3, line 19, "'146833'" should read --'FLOR146833'--

At Col. 3, line 21, "'146833'" should read --'FLOR146833'--

At Col. 3, line 23, "'146833'" should read --'FLOR146833'--

At Col. 3, line 25, "'146833'" should read --'FLOR146833'--

At Col. 3, line 29, "'146833'" should read --'FLOR146833'--

At Col. 3, line 36, "'146833'" should read --'FLOR146833'--

At Col. 3, line 40, "'146833'" should read --'FLOR146833'--

At Col. 3, line 41, "'146833'" should read --'FLOR146833'--

At Col. 3, line 43, "'146833'" should read --'FLOR146833'--

At Col. 3, line 46, "'146833'" should read --'FLOR146833'--

At Col. 3, line 53, "'146833'" should read --'FLOR146833'--

IN THE CLAIMS:

At Col. 6, line 32, In claim 1, "'146833'" should read --'FLOR146833'--